US008118799B2

(12) United States Patent
Datta et al.

(10) Patent No.: US 8,118,799 B2
(45) Date of Patent: Feb. 21, 2012

(54) DISPOSABLE GARMENT HAVING FIRST AND SECOND ATTACHMENT MEMBERS

(75) Inventors: Paul Joseph Datta, Appleton, WI (US); Barbara Ann Gossen, Oshkosh, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 1922 days.

(21) Appl. No.: 10/430,655

(22) Filed: May 5, 2003

(65) Prior Publication Data
US 2004/0225271 A1    Nov. 11, 2004

(51) Int. Cl.
*A61F 13/15* (2006.01)
(52) U.S. Cl. ............... 604/385.11; 604/385.01
(58) Field of Classification Search ............. 604/385.11, 604/358, 385.01; 383/200, 209, 210
See application file for complete search history.

(56) References Cited

U.S. PATENT DOCUMENTS

| 3,692,618 | A |  | 9/1972 | Dorschner et al. |
| 3,849,241 | A |  | 11/1974 | Butin et al. |
| 4,340,563 | A |  | 7/1982 | Appel et al. |
| 4,619,649 | A |  | 10/1986 | Roberts |
| 4,720,415 | A |  | 1/1988 | Vander Wielen et al. |
| 5,366,793 | A |  | 11/1994 | Fitts et al. |
| 5,624,420 | A | * | 4/1997 | Bridges et al. ............ 604/365 |
| 5,695,868 | A |  | 12/1997 | McCormack |
| 6,036,805 | A |  | 3/2000 | McNichols |
| 6,287,287 | B1 |  | 9/2001 | Elsberg |
| 6,322,552 | B1 |  | 11/2001 | Blenke et al. |
| 6,325,542 | B1 | * | 12/2001 | Komatsu ..................... 383/210 |
| 6,402,731 | B1 |  | 6/2002 | Suprise et al. |
| 6,454,752 | B1 |  | 9/2002 | Huang et al. |
| 6,508,797 | B1 |  | 1/2003 | Pozniak et al. |
| 6,524,293 | B1 |  | 2/2003 | Elsberg et al. |
| 6,551,294 | B1 |  | 4/2003 | Elsberg et al. |
| 6,572,601 | B2 |  | 6/2003 | Suprise et al. |
| 6,579,275 | B1 |  | 6/2003 | Pozniak et al. |
| 6,752,796 | B2 |  | 6/2004 | Karami |
| 2001/0049516 | A1 | * | 12/2001 | Shimada et al. ......... 604/385.11 |

(Continued)

FOREIGN PATENT DOCUMENTS

| GB | 2267024 | * | 5/1993 |
| GB | 2 267 024 A |  | 11/1993 |
| WO | WO 00/37010 A1 |  | 6/2000 |

(Continued)

OTHER PUBLICATIONS

American Society for Testing Materials (ASTM) Designation: D 5733-99, "Standard Test Method for Tearing Strength of Nonwoven Fabrics by the Trapezoid Procedure," pp. 1-6, published Jan. 2000.

*Primary Examiner* — Lynne Anderson
(74) *Attorney, Agent, or Firm* — H. Michael Kubicki

(57) ABSTRACT

A disposable garment for absorbing human exudate is disclosed having a first attachment member and a pair of second attachment members. The garment has a front panel, a back panel and a crotch region therebetween. The garment is folded to enable the pair of second attachment members to be secured to the first attachment member and form a waist opening and a pair of leg openings. A pair of frangible sections is formed in the first attachment member at locations outboard of the side edges of the front panel. Each of the second attachment members can bridge across one of the frangible sections and be removeably secured to the first attachment member to form an easy to open disposable garment.

37 Claims, 3 Drawing Sheets

U.S. PATENT DOCUMENTS

| | | |
|---|---|---|
| 2002/0165518 A1 | 11/2002 | Datta et al. |
| 2002/0173768 A1 | 11/2002 | Elsberg et al. |
| 2002/0183712 A1 | 12/2002 | Datta et al. |
| 2003/0055389 A1 | 3/2003 | Sanders et al. |
| 2003/0125702 A1 * | 7/2003 | Couture-Dorschner et al. ............... 604/387 |
| 2003/0135192 A1 | 7/2003 | Guralski et al. |

FOREIGN PATENT DOCUMENTS

| | | |
|---|---|---|
| WO | WO 00/37010 A1 * | 6/2000 |
| WO | WO 0037010 A1 * | 6/2000 |
| WO | WO 02/36060 A2 | 5/2002 |
| WO | WO 02/069867 A | 9/2002 |
| WO | WO 03/024372 A2 | 3/2003 |
| WO | WO 03/028604 A1 | 4/2003 |

* cited by examiner

DISPOSABLE GARMENT HAVING FIRST AND SECOND ATTACHMENT MEMBERS

BACKGROUND OF THE INVENTION

Disposable garments for absorbing human exudate can appear similar in size and shape to regular cloth underwear which is designed to be laundered and reused two or more times. A disposable garment is an article intended to be worn by persons, including infants, toddlers, or adults, that is designed for single use or temporary use and is meant to be disposed of after being used once instead of being laundered or dry cleaned for re-use. Some examples of disposable garments include infant diapers, training pants, adult incontinence garments, feminine pants, etc.

Some disposable garments manufactured today resemble regular cloth underwear in that they have a waist opening and a pair of leg openings. Such disposable garments can be pulled up around the torso of a user in a similar fashion as regular cloth underwear. Still other disposable garments contain an attachment mechanism that will allow the garment to be opened into a flat configuration prior to being placed around the torso of a user. This design is beneficial for bed bound users who may be immobile or who may need assistance in securing the garment in place. Still other disposable garments contain attachment means for opening and closing the waist opening after the garment has been positioned around the torso of a user. This feature is advantageous in that the user does not have to undress when there is a desire to check the status of the disposable garment. One disposable garment currently being commercially sold uses a pair of perforation lines that extend from the waist opening to one of the respective leg openings. The perforation lines are designed to be broken either prior to positioning the garment around the user's torso or while the garment is already positioned about the user's torso. A pair of attachment members is then utilized to refasten the garment so that it is snug about the user's torso. This commercial design can be improved to make it easier for the user to break open the product. Especially for older adults, some of who may be suffering from arthritis, an easier means of breaking open the product is desirable.

Now a disposable garment for absorbing human exudate has been invented that uses a pair of frangible sections that are formed such that they can be broken very easily.

SUMMARY OF THE INVENTION

Briefly, this invention relates to a disposable garment for absorbing human exudate. The garment includes a front panel and a back panel. The front panel has a pair of side edges and a first attachment member secured to it that extends beyond the pair of side edges. The back panel has a pair of tabs each containing a second attachment member. The garment also includes an absorbent assembly secured to the front and back panels. The absorbent assembly is folded to enable the first attachment member to be secured to the pair of tabs to form a garment having a waist opening and a pair of leg openings. A pair of frangible sections is formed in the first attachment member at locations outboard of the pair of side edges of the front panel. Each of the frangible sections extends across the width of the first attachment member. The pair of tabs can be folded to allow each of the second attachment members to bridge across one of the frangible sections and be removeably secured to the first attachment member to form an easy to open disposable garment. As the tabs are pulled open, the second attachment members will separate from the first attachment member and the pair of frangible sections will tear open allowing the user to inspect the interior of the disposable garment. The disposable garment can then be refastened by folding the tabs inward such that the second attachment members again engage with the first attachment member.

DETAILED DESCRIPTION

Figure 1:
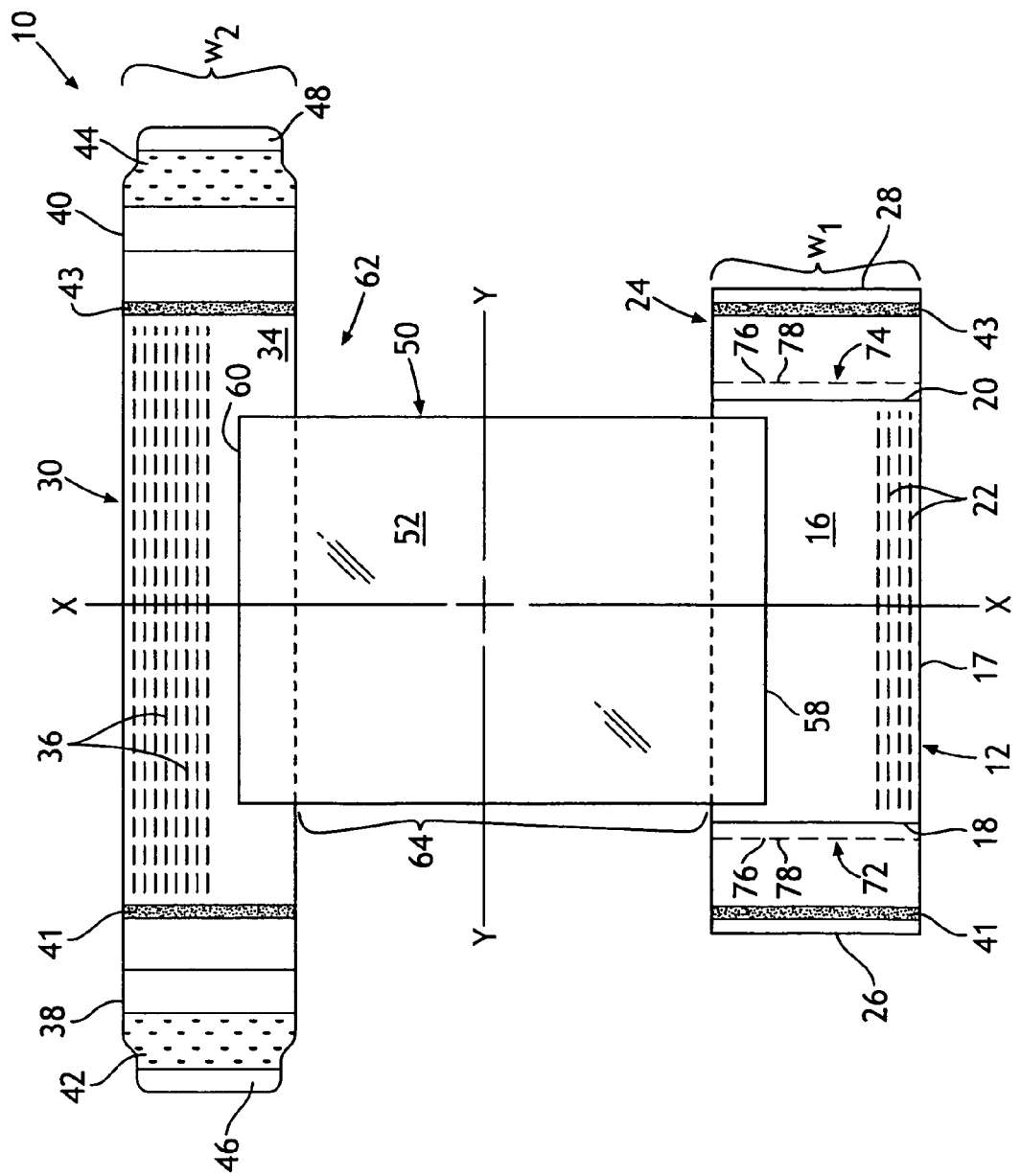
FIG. 1 is a plane view of a disposable garment shown in an open configuration.
Figure 2:
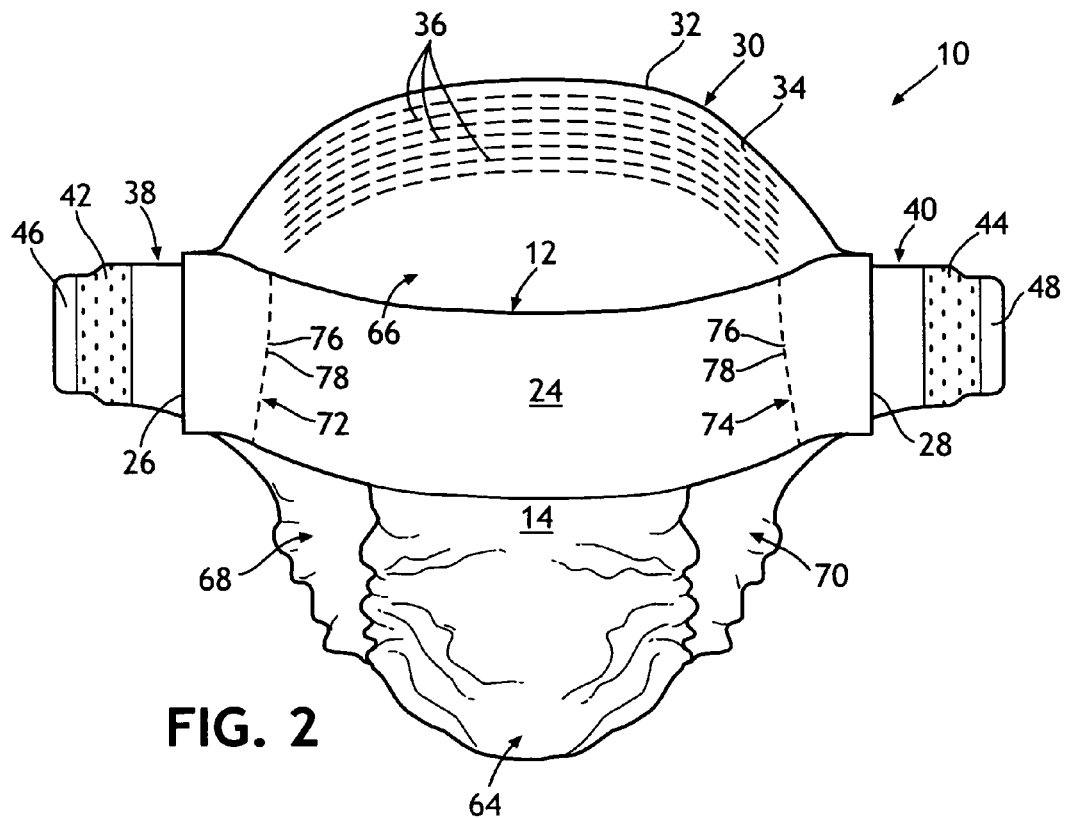
FIG. 2 is a perspective view of the disposable garment shown in FIG. 1 after the first attachment member is secured to the back panel to form a waist opening and a pair of leg openings.

Referring to FIGS. 1 and 2, a disposable garment 10 is shown for absorbing human exudate. The human exudate can include urine, menses, or other bodily fluids, as well as semi-solid and solid excrement. The disposable garment 10 can be constructed as an adult incontinence product, an infant diaper, a child training pant, a menstrual pant, etc. By "disposable" it is meant an article that is designed for single use or temporary use and is meant to be disposed of after being used once instead of being laundered or dry cleaned for re-use. The disposable garment 10 can be pulled up around a human torso much like regular cotton underwear or it can be opened into a flat configuration, be positioned about the torso, and then be fastened in place.

Still referring to FIGS. 1 and 2, the disposable garment 10 includes a front panel 12 having a first surface 14 and a second surface 16. The first surface 14 can be the exterior surface and the second surface 16 can be the interior surface of the disposable garment 10. The first or exterior surface 14 faces away from the human body when the disposable garment 10 is worn and the second or interior surface 16 faces and contacts the body when the disposable garment 10 is worn. The front panel 12 also has an outer end 17 and a pair of spaced apart side edges 18 and 20. The front panel 12 can be formed from a woven or nonwoven material. The material can be constructed from natural or synthetic fibers. The front panel 12 can also be constructed from a breathable material which will allow vapors to escape while retaining liquid and solid exudate. Desirably, the material will have a soft feel since it will contact the stomach region of the human body. It is also advantageous for the front panel 12 to exhibit extensible properties which will allow it to stretch and/or contract in at least one direction. For example, the front panel 12 can be formed from an elastic material or from a conformable knit material. Desirably, the extensible properties will allow the front panel 12 to stretch and/or contract in a transverse direction extending across the front of the wearer's torso from the left hip bone to the right hip bone. Materials from which the front panel 12 can be formed include spunbond, meltblown, films apertured films woven fabrics and a bonded carded web. "Spunbond" is manufactured and sold commercially by Kimberly-Clark Corporation having an office at 401 North Lake Street, Neenah, Wis. 54956. A "bonded carded web" is commercially available from several vendors. Spunbond is described in U.S. Pat. No. 4,720,415 issued to Vander Wielen et al. and spunbond filaments and related manufacturing processes are described in U.S. Pat. No. 4,340,563 issued to Appel et al. and U.S. Pat. No. 3,692,618 issued to Dorschner et al. Meltblown fibers and a process used to make them are taught in U.S. Pat. No. 3,849,241 issued to Butin et al. All of the above-identified patents are incorporated and made a part hereof.

The front panel 12 can also be formed as a laminate having two or more layers. Desirably, one of the layers forming the laminate is an elastic layer. By "elastic" it is meant any material which, upon application of a biasing force, is stretchable, that is, elongatable at least 60 percent (i.e., to a stretched, biased length which is at least about 160 percent of its relaxed unbiased length), and which, will recover at least 55 percent of its elongation upon release of the stretching, elongating force. A hypothetical example would be a one (1) inch sample of a material which is elongated to at least 1.60 inches and which, upon being elongated to 1.60 inches and released, will recover to a length of not more than 1.27 inches. Many elastic materials may be elongated by much more than 60 percent (i.e., much more than 160 percent of their relaxed length), for example, elongated 100 percent or more, and many of these will recover to substantially their initial relaxed length, for example, to within 105 percent of their original relaxed length, upon release of the stretching force.

Alternatively, the front panel 12 can be formed from one or more elastic strands 22 sandwiched between two outer layers. Desirably, a plurality of elastic strands 22 will be incorporated into a laminate structure so as to function as a portion of a waist band. From two to ten elastic strands 22 are normally utilized in the front panel 12. When elastic strands 22 are utilized, as shown in FIG. 1, the elastic strands 22 should be aligned parallel to one another and be spaced apart a predetermined distance. The elastic strands 22 can vary in cross-sectional configuration and can be round, semi-circular, square, rectangular, oval, or of any other shape. The elastic strands 22 can be uniformly or randomly spaced apart. Some of the elastic strands 22 can even cross over one another, if desired. The elastic strands 22 can be formed from LYCRA®. LYCRA® is a registered trademark of E.I. Du Pont De Nemours & Co. having an office at 1007 Market Street, Wilmington, Del. 19898. The diameter and/or cross-sectional configuration of the elastic strands 22, the decitex (weight in grams per 10,000 meters of a strand) of the elastic strands 22, and the tension imparted into the elastic strands 22 can all be varied to suit one's particular product needs. Other elastic options suitable for this invention include elastic films or foams.

A first attachment member 24 is secured to the first or exterior surface 14 of the front panel 12 and extends laterally beyond the pair of side edges 18 and 20. The first attachment member 24 can be coterminous with the outer end 17 of the front panel 12 or can extend above or below this outer end 17 if desired. The first attachment member 24 can vary in configuration and construction. Desirably, the first attachment member 24 will be a female fastener. For example, the first attachment member 24 can be one or more loops into which a male fastener, like one or more hooks, can engage. More desirably, the first attachment member 24 is a material containing a plurality of loops into which a plurality of hooks can engage.

The first attachment member 24 can be secured or permanently attached to the front panel 12 by one or more types of fasteners. Such fasteners can include hot or cold melt adhesives, ultrasonics, or a mechanical fastener, such as by thread, by stitching, by a mechanical clasp, by a button and button hole, or by the application of heat, pressure, or heat and pressure. Other types of fasteners can also be used that are known to those skilled in the fastening art. The first attachment member 24 can be secured along a portion of the front panel 12, along its entire length or over its entire surface area.

The first attachment member 24 has a first side edge 26 spaced apart from a second side edge 28. The first attachment member 24 also has a width ($w_1$), see FIG. 1. The width ($w_1$) of the first attachment member 24 can be equal to or greater than about 0.5 inches (about 1.2 centimeters (cm)). Desirably, the width ($w_1$) of the first attachment member 24 ranges from about 0.5 inch (about 1.2 cm) to about 15 inches (about 38 cm). More desirably, the width ($w_1$) of the first attachment member 24 ranges from about 1 inch (about 2.5 cm) to about 10 inches (about 25 cm). Most desirably, the width ($w_1$) of the first attachment member 24 ranges from about 1.5 inches (about 3.8 cm) to about 8 inches (about 20 cm). By increasing the width ($w_1$) of the first attachment member 24, one can cover a greater portion of the stomach region of the wearer as well as permitting the front panel 12 to be positioned over the hip bones of the wearer. These two characteristics can provide for a better fitting disposable garment 10 that will stay in place even when the wearer walks, runs, sits, bends over, kneels down, etc.

The disposable garment 10 also includes a back panel 30 that can be spaced apart from the front panel 12. The back panel 30 has a first surface 32; see FIG. 2, and a second surface 34. The first surface 32 can be the exterior surface and the second surface 34 can be the interior surface of the disposable garment 10. The first or exterior surface 32 faces away from the human body when the disposable garment 10 is worn and the second or interior surface 34 faces and contacts the body when the disposable garment 10 is worn. The back panel 30 can be formed from a woven or nonwoven material. The material can be constructed from natural or synthetic fibers. The back panel 30 can also be constructed from a breathable material which will allow vapors to escape while retaining liquid and solid exudate. Desirably, the material will have a soft feel since it will contact the buttock region of the human body. It is also advantageous for the back panel 30 to exhibit extensible properties which will allow it to stretch and/or contract in at least one direction. Desirably, the extensible properties will allow the back panel 30 to stretch and/or contract in a transverse direction extending across the lower back of the wearer's torso from the left hip bone to the right hip bone. The back panel 30 can be formed from an elastic material as was described above with reference to the front panel 12. Materials from which the back panel 30 can be formed include spunbond, meltblown and a bonded carded web. "Spunbond" is manufactured and sold commercially by Kimberly-Clark Corporation having an office at 401 North Lake Street, Neenah, Wis. 54956. "Meltblown" and a "bonded carded web" are commercially available from several vendors.

The back panel 30 can also be formed as a laminate having two or more layers. Desirably, one of the layers forming the laminate is an elastic layer. The term "elastic" has been defined above with reference to the discussion on the front panel 12. Alternatively, one or more elastic strands 36 can be sandwiched between two outer layers. Desirably, a plurality of elastic strands 36 will be incorporated into a laminate structure so as to function as a portion of a waist band. When elastic strands 36 are utilized, as shown in FIG. 1, the elastic strands 36 should be aligned parallel to one another and be spaced apart a predetermined distance. The elastic strands 36 can vary in cross-sectional configuration and can be round, semi-circular, square, rectangular, oval, or of any other shape. The elastic strands 36 can be uniformly or randomly spaced apart. Some of the elastic strands 36 can even cross over one another, if desired. The elastic strands 36 can be formed from LYCRA®. LYCRA® is a registered trademark of E.I. Du Pont De Nemours & Co. having an office at 1007 Market Street, Wilmington, Del. 19898. The diameter and/or cross-sectional configuration of the elastic strands 36, the decitex (weight in grams per 10,000 meters of a strand) of the elastic strands 36, and the tension imparted into the elastic strands 36 can all be varied to suit one's particular product needs.

The back panel 30 will normally contain more elastic strands 36 than are present in the front panel 12. From 10 to about 30 elastic strands 36 can be present in the back panel 30 depending upon the overall size and use of the disposable garment. Since the back panel 30 is designed to cover a portion of the lower back of the wearer along with the hip and buttock regions, a larger number of elastic strands 36 will provide for a better fit to the human body. The extra elastic strands 36 situated in the back panel 30 will also assist in preventing the disposable garment 10 from slipping or creeping downward on the torso especially once the disposable garment 10 is filled with body waste.

The back panel 30 also has a pair of tabs 38 and 40 that can be integrally formed with the remainder of the back panel 30. Each of the tabs 38 and 40 extend outward in opposite directions from the back panel 30. Desirably, the tabs 38 and 40 extend laterally outward from the remainder of the back panel 30. The size and configuration of each of the tabs 38 and 40 can vary to suit one's particular needs. Desirably, both of the tabs 38 and 40 will be a mirror image of the other but differently sized and shaped tabs can be utilized, if required.

Each of the tabs 38 and 40 contains a second attachment member, 42 and 44 respectively, located on the second or interior surface 34. The second attachment members 42 and 44 can vary in construction. Desirably, the second attachment members 42 and 44 will each be a male fastener. For example, the second attachment members 42 and 44 can be a plurality of hooks that will easily engage into the female fastener of the first attachment member 24. A VELCRO® hook and loop fastening mechanism can be employed. VELCRO® is a registered trademark of Velcro USA, Inc. having an office at 406 Brown Avenue, Manchester, N.H. 03103. Alternatively, the second attachment members 42 and 44 can be constructed from a releasable adhesive or other mechanical fastener known to those skilled in the art.

It should be noted that if one desired to construct the first attachment member 24 as a male fastener, then the second attachment members 42 and 44 would be constructed as a female fastener.

The second attachment members 42 and 44 can be spaced apart from the distal ends of the tabs 38 and 40 so as to provide finger grasping regions 46 and 48. The finger grasping regions 46 and 48 can vary in size and dimension but should be of sufficient area to allow the wearer of the disposable garment 10 to easily grasp the tabs 38 and 40 and pull then outward into an open position.

Still referring to FIG. 1, each of the tabs 38 and 40 has a width ($w_2$) that can be less than, equal to or greater than the width ($w_1$) of the first attachment member 24. Desirably, the width ($w_2$) of each of the tabs 38 and 40 is less than the width ($w_1$) of the first attachment member 24. The reason for this will be explained shortly when describing the interaction of the tabs 38 and 40 with the first attachment member 24.

Figure 3:
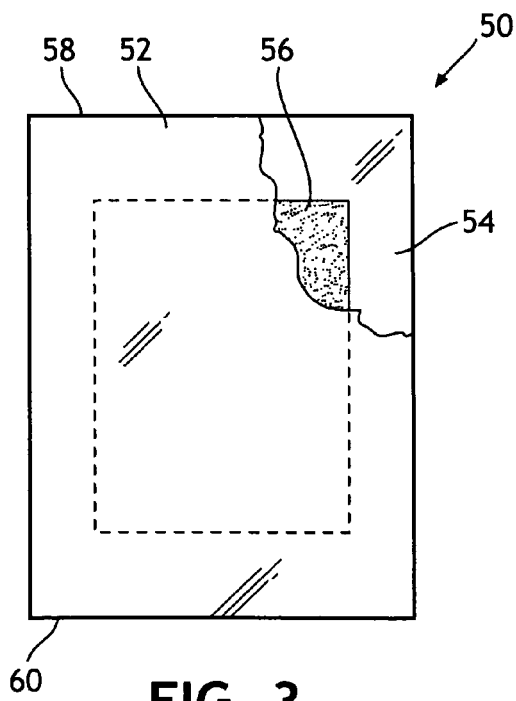
FIG. 3 is a top view with a partial cut away portion exposing the construction of the absorbent assembly.

Referring now to FIG. 3, the disposable garment 10 also includes an absorbent assembly 50. The absorbent assembly 50 is constructed of a liquid pervious bodyside liner 52, a liquid-impervious outer cover 54, and an absorbent 56 positioned between and enclosed by the bodyside liner 52 and the outer cover 54. The liquid pervious bodyside liner 52 is located nearest to the human body, adjacent to the skin of the user, and can be formed from a woven or non-woven material that will readily allow liquid or fluids to past therethrough. The bodyside liner 52 is normally a very thin web that can be formed from natural or synthetic fibers, with or without apertures formed therein. A spunbond, meltblown, apertured film and a bonded carded web are materials that work well as a bodyside liner 52.

The liquid-impervious outer cover 54 is located on the exterior of the disposable garment 10, away from the skin of the user. The liquid-impervious outer cover 54 is formed from a material which will restrict fluid from penetrating or passing therethrough so as to prevent the outer clothing of the wearer from becoming soiled. Desirably, the outer cover 54 has a soft feel so as not to chafe the inner thighs of the wearer. The outer cover 54 can also be formed from natural or synthetic fibers. The outer cover 54 can be formed from a material that is not noisy when squeezed or wrinkled so that the disposable garment 10 remains discreet. The outer cover 54 can also be formed from a breathable material that will allow vapors to exit the absorbent assembly 50 while retaining bodily fluids and solids. The outer cover 54 can further be formed from a laminate where one layer of the laminate is liquid-Impervious. Examples of various materials that can be used as the outer cover 54 include a polyolefin, such as polypropylene or polyethylene; a liquid impervious layer bonded to a spunbond; and a thermoplastic material bonded to a spunbond. Other materials known to those skilled in the art can also be utilized. An example of a liquid-impervious layer is a breathable film as taught in U.S. Pat. No. 5,695,868 issued to McCormack and assigned to Kimberly-Clark Worldwide Inc.

The absorbent 56 is enclosed and desirably sealed within the liquid pervious bodyside liner 52 and the liquid-impervious outer cover 54. The absorbent 56 can be formed from natural or synthetic materials. The absorbent 56 can be made from cellulosic fibers, wood pulp, textile fibers or other absorbent materials known to those skilled in the art. Superabsorbents, in solid form and in the shape of small particles, granules, flakes, fibers, etc. can be mixed in with the absorbent material to increase the absorbent capacity of the absorbent 56.

Referring again to FIG. 1, the absorbent assembly 50 further includes a first end 58 and a second end 60. The absorbent assembly 50 is secured to the front panel 12 approximate the first end 58 and is secured to the back panel 30 approximate the second end 60. The absorbent assembly 50 can be secured to the front and back panels, 12 and 30 respectively, in a permanent fashion or in a removable fashion to enable a replacement assembly to be later substituted. The first and second ends, 58 and 60 respectively, can be secured to the front and back panels, 12 and 30 respectively, by any means known to those skilled in the art. Some examples of attachment means include the use of an adhesive, co-adhesives, glue, ultrasonics, stitching using thread, a thermal bond, a pressure bond, and a heat and pressure bond. Mechanical attachment means, such as buttons and button holes, snaps, swivels, as well as various types of engagement members can also be used. The exact distance the first and second ends, 58 and 60 respectively, overlap or are spaced into the front and back panels, 12 and 30 respectively, can vary to optimize the functionality of the disposable garment 10. For example, the overlap can range from 0.25 inches (about 6 mm) to about 2 inches (about 51 mm). The exact amount of overlap will depend on a number of factors, including the size of the garment, the anatomy of the wearer of the garment, for example, an infant versus an adult, and the amount of body fluid that is meant to be absorbed by the garment. These and other factors will dictate the actual amount of overlap that suits one's particular needs.

The absorbent assembly 50 can be secured to the first surfaces, 14 and 32, of the front and back panels, 12 and 30 respectively, or to the second surfaces, 16 and 34 of the front and back panels, 12 and 30 respectively. Desirably, the absorbent assembly 50 is secured to the first surfaces, 14 and 32, of the front and back panels, 12 and 30 respectively, for this tends to form a more aesthetically pleasing garment.

It should be noted that the distance the second end 60 of the absorbent assembly 50 overlaps a portion of the width ($w_1$) of the front panel 12 can be less than, equal to or greater than the distance that the first end 58 of the absorbent assembly 50 overlaps the width ($w_2$) of the back panel 30. When the disposable garment 10 is designed to be worn by active wearers, the absorbent assembly 50 can be positioned such that the second end 60 extends into the width ($w_1$) of the front panel 12 approximately the same distance that the first end 58 extends into the width ($w_2$) of the back panel 30. When the disposable garment 10 is designed to be worn by bedridden persons, the absorbent assembly 50 can be positioned such that the second end 60 extends into the width ($w_1$) of the front panel 12 a shorter distance than the first end 58 extends into the width ($w_2$) of the back panel 30. This shift in position of the absorbent assembly 50 can provide added protection against leakage of body fluid from a person lying in a recumbent manner. For many disposable garments, the back panel has a greater width ($w_2$) than the width ($w_1$) of the front panel. Therefore, the distance the second end 60 extends into the width ($w_1$) of the front panel 12 can be greater than the distance that the first end 58 extends into the back panel 30. This arrangement allows the absorbent assembly 50 to be skewed more towards the front of the disposable garment 10 and function better for both male and female users. It should be noted that the width ($w_1$ and $w_2$) of the front and back panels, 12 and 30 respectively, impacts on the exact points of attachments of the absorbent assembly 50 to the front and back panels, 12 and 30 respectively.

Still referring to FIG. 1, when the front panel 12, the absorbent assembly 50 and the back panel 30 are attached together, a chassis 62 is formed having a longitudinal central axis X-X and a transverse central axis Y-Y. A crotch region 64 is located between the front panel 12 and the back panel 30. The crotch region 64 is designed to contact the crotch of the wearer and can vary in length (measured along the X-X axis) depending upon the size of the disposable garment 10 and the size of the person the garment 10 is manufactured for. For example, for an infant diaper, the crotch region 64 can vary from about 6 inches (about 15 cm) to about 14 inches (about 36 cm). For an adult incontinence garment, the crotch region 64 can vary from about 8 inches (about 20 cm) to about 30 inches (about 76 cm).

Referring again to FIGS. 1 and 2, the absorbent assembly 50 is capable of being folded along the transverse central axis Y-Y to enable the first and second side edges, 26 and 28 respectively, of the first attachment member 24 to be secured to the pair of tabs 38 and 40. The attachment occurs at bond areas 41 and 43. The exact means of attaching or securing the first and second side edges, 26 and 28 respectively, of the first attachment member 24 to the pair of tabs 38 and 40 can vary. Adhesives, ultrasonics bonds, thermal bonds, heat bonds, pressure bonds and interlocking members, as well as other means known to those skilled in the art, can be used to form the bonds. The area of attachment can be a single line or an area having a predetermined width.

When the first attachment member 24 is secured to the pair of tabs 38 and 40, a disposable garment 10 is formed having a waist opening 66 and a pair of leg openings 68 and 70. The width ($w_1$) of the first attachment member 24 can extend from the waist opening 66 to the pair of leg openings 68 and 70.

The disposable garment 10 further includes a pair of frangible sections 72 and 74 that are formed in the first attachment member 24. Each frangible section, 72 and 74, can be a perforation line, a pre-stressed or thinned section of material, a score line, a section of different, weaker material, or other configurations adapted to be readily torn or broken in order to separate the material. Each frangible section, 72 and 74, need not extend entirely across an area of the disposable garment 10 but may desirably be present in a degree sufficient to allow the appropriate material, as well as adjacent material, to be torn or broken. In the drawings, the pair of frangible sections, 72 and 74, is depicted as perforation lines.

The pair of frangible sections 72 and 74 are located outboard of the pair of side edges 18 and 20 of the front panel 12. Desirably, the pair of frangible sections 72 and 74 are located between one of the pair of side edges 18 and 20 of the front panel 12 and one of the first and second side edges, 26 and 28 respectively, of the first attachment member 24. More desirably, the pair of frangible sections 72 and 74 is located between one of the pair of side edges 18 and 20 of the front panel 12 and one of the bond areas 41 and 43. Each of the frangible sections 72 and 74 can extend across at least half of the width ($w_1$) of the first attachment member 24. Desirably, each of the frangible sections 72 and 74 extends across a majority of the width ($w_1$) of the first attachment member 24. Most desirably, each of the pair of frangible sections 72 and 74 extends across the width ($w_1$) of the first attachment member 24 from the waist opening 66 to one of the respective leg openings 68 and 70. The pair of frangible sections 72 and 74 can have a linear or a non-linear configuration. Examples of non-linear configurations include: an arcuate shape, a curved shape, a saw-toothed shape, a sinusoidal shape, a zigzag shape, or any other shape desired.

Each of the pair of frangible sections 72 and 74 may be formed of intermittent strength along its length by making some areas stronger than other areas. This feature could assist in assuring that the pair of frangible sections 72 and 74 will not tear prematurely when the disposable garment 10 is pulled up around the wearer's torso. This feature can also assure that the pair of frangible sections 72 and 74 is easily broken in order to start the opening process.

It should be noted that it may be advantageous to forming the pair of frangible sections 72 and 74 in the first attachment member 24 before the absorbent assembly 50 is folded. Desirably, the first attachment member 24 is perforated before the front panel 12 is secured to the absorbent assembly 50.

Each of the pair of frangible sections 72 and 74 is tearable or breakable by applying a minimum amount of pressure across the pair of frangible sections 72 and 74. It should be noted that the pair of frangible sections 72 and 74 can be simultaneously broken or torn. Each of the frangible sections 72 and 74 can consist of multiple land areas 76 aligned adjacent to open areas 78. The length of each of the land areas 76 can be less than, equal to, or be greater than the length of each of the open areas 78. The ratio between the length of a land to an open area, 76 and 78 respectively, can be adjusted to increase or decrease the amount of force required to break the pair of frangible sections 72 and 74. The type of material into which the pair of frangible sections 72 and 74 are formed, the thickness of the material, the configuration of the pair of frangible sections 72 and 74, as well as other features, will all have an impact on the amount of force needed to break the pair of frangible sections 72 and 74. It should also be noted that the amount of force needed to start to break each of the pair of frangible sections 72 and 74 may be slightly greater than the amount of force needed to continue to tear open the pair of frangible sections 72 and 74.

The frangible sections 72 and 74 can be formed such that each of the land areas 76 has a length that is equal to the length of each of the open areas 78. Alternatively, the length of the land and/or open areas, 76 and 78 respectively, can vary along a portion of or over the total length of the pair of frangible sections 72 and 74. It has been found that when the length of the open areas 78 is greater than the length of the land areas 76, that the pair of frangible sections 72 and 74 can be easily broken. It is important to design the land and open areas, 76 and 78 respectively, such that the pair of frangible sections 72 and 74 is easy for the user to break yet ensure that they will not break prematurely. Good results have been obtained by dimensioning the length of each of the open areas 78 to be at least two times greater than the length of each of the land areas 76. Desirably, the length of each of the open areas 78 will be at least three times greater than the length of each of the land areas 76. More desirably, the length of each of the open areas 78 will be at least four times greater than the length of each of the land areas 76.

The amount of force required to tear open the frangible sections 72 and 74 will be very important to the user of the disposable garment 10. The pair of frangible sections 72 and 74 need to remain unbroken while the disposable garment 10 is pulled up around the torso of the user. However, the pair of frangible sections 72 and 74 must be easy to open when the user wants to open and/or remove the disposable garment 10. The tear strength of the pair of frangible sections 72 and 74 should be less than about 3,000 grams when tested using peak load according to ASTM test procedure D-5733-99. More desirably, the tear strength of the pair of frangible sections 72 and 74 should be less than about 2,000 grams. Most desirably, the tear strength of the pair of frangible sections 72 and 74 should range from between about 100 grams to about 500 grams. A tear strength of about 400 grams works well for diapers designed to be worn by infants.

When conducting the peak load test for tear strength for each of the frangible sections 72 and 74, according to ASTM D-5733-99, one should prepare each sample by placing the slot line formed in the template over one of the frangible sections 72 or 74. The slot line formed in the template should be centered over one of the frangible sections 72 or 74 to assure that the pattern, for example, a perforation pattern is centered along the slot line.

Referring again to FIG. 1, each of the tabs 38 and 40 can be folded forward over the first attachment member 24. This folding action will permit each of the second attachment members, 42 and 44, to bridge across one of the pair of frangible sections 72 and 74 and be removeably secured to the first attachment member 24. The disposable garment 10 will now be in a normal wearing condition. In order to open the disposable garment 10, the wearer simply has to seize the finger grasping regions 46 and 48 of the tabs 38 and 40, either sequentially or simultaneously, and pull the tabs 38 and 40 to an open position. The wearer can seize each of the finger grasping regions 46 and 48 between his or her thumb and index finger and pull the tabs 38 and 40 outward and laterally apart. This action will apply a force across the pair of frangible sections 72 and 74 and they will tear open. The wearer can then inspect the disposable garment 10 to see if it can still be used for a longer period of time or can remove and dispose of it if the disposable garment 10 is soiled. If the garment 10 can still be used, the wearer can simply fold the tabs 38 and 40 back over the first attachment member 24 and press the pair of second attachment members 42 and 44 against the first attachment member 24. This engagement will provide a refastened disposable garment 10 for providing the user with continued protection.

Figure 4:
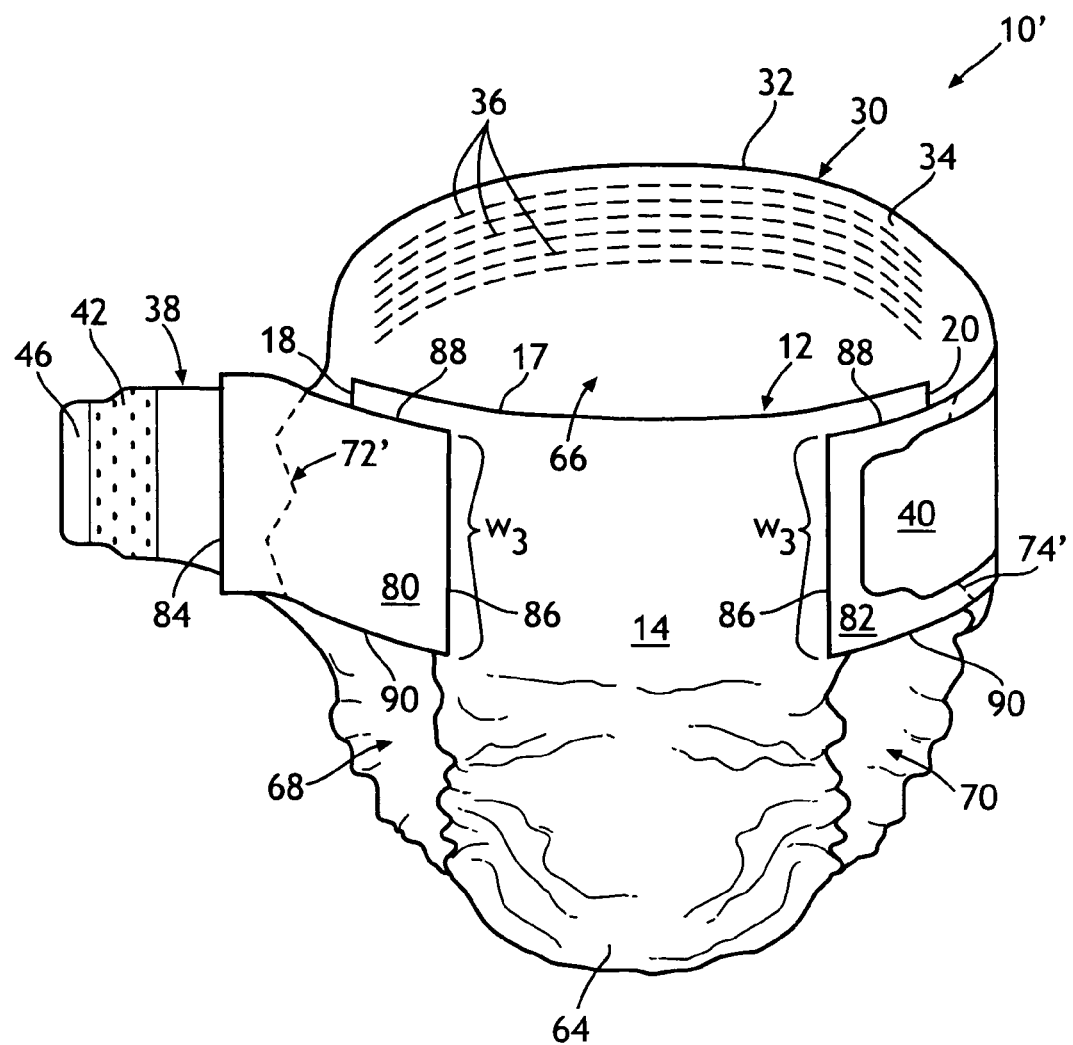
FIG. 4 is a perspective view of an alternative embodiment of a disposable garment showing a pair of first attachment members.

Referring now to FIG. 4, an alternative embodiment of a disposable garment 10' is shown that is similar to the embodiment depicted in FIG. 2 except for three differences. The first difference is that the first attachment member 24 has been replaced with a pair of first attachment members 80 and 82. The pair of first attachment members 80 and 82 is secured to the first or exterior surface 14 of the front panel 12 and each member 80 and 82 extends beyond one of the pair of side edges 18 and 20 of the front panel 12. The pair of first attachment members 80 and 82 is spaced apart from one another and together they can be smaller or equal in surface area to the single attachment member 24, shown in FIG. 2. Desirably, the pair of first attachment members 80 and 82 is smaller in surface area than the single attachment member 24. The pair of first attachment members 80 and 82 can be spaced apart by at least about 2 inches (about 5 cm), desirably, by at least about 3 inches (about 7.5 cm), and most desirably, by at least about 4 inches (about 10 cm). The pair of first attachment members 80 and 82 can have a length, measured parallel to the transverse central axis Y-Y, of from between about 1 inch (about 2.5 cm) to about 12 inches (about 30 cm). Desirably, the pair of first attachment members 80 and 82 can have a length of from between about 2 inches (about 5 cm) to about 8 inches (about 20 cm). Most desirably, the pair of first attachment members 80 and 82 can have a length of about 6 inches (about 15 cm) or less. Each of the pair of first attachment members 80 and 82 can have a width ($w_3$). Each of the pair of first attachment members 80 and 82 has a first side edge 84, a second side edge 86, an upper edge 88 and a lower edge 90. Each of the first side edges 84 is permanently secured to one of the tabs 38 and 40 and each of the second side edges 86 is permanently secured to the front panel 12 to form the disposable garment 10' having a waist opening 66 and a pair of leg openings 68 and 70.

A second difference in the disposable garment 10' is that the upper edge 88 of the pair of first attachment members 80 and 82 does not extend above or beyond the outer end 17 of the front panel 12. Instead, a space or gap of at least about 0.12 inches (about 0.3 cm) is present. In this embodiment, a portion of the front panel 12 is clearly visible above the pair of first attachment members 80 and 82. This feature can create an aesthetically pleasing disposable garment 10'.

The third difference in the disposable garment 10' is that the pair of linear frangible sections 72 and 74, shown in FIG. 2, have been replaced by a pair of non-linear frangible sections 72' and 74'. Each of the pair of non-linear frangible sections 72' and 74' has a zigzag profile and each extends from the upper edge 88 to the lower edge 90 thereby spanning across the entire width ($w_3$) of each of the members 80 and 82. Each of the pair of first attachment members 80 and 82 extends from a point below the waist opening 66 to one of the pair of leg openings 68 and 70. Each of the pair of frangible sections 72' and 74' are situated outboard of the pair of side edges 18 and 20 of the front panel 12. Desirably, each of the pair of frangible sections 72' and 74' are located between one of the pair of side edges 18 and 20 of the front panel 12 and one of the bond areas 41 and 43. More desirably, each of said pair of frangible sections 72' and 74' is positioned laterally inward from one of the bond areas 41 and 43. This arrangement permits the pair of frangible sections 72' and 74' to be broken or torn open as the tabs 38 and 40 are pulled away from the first attachment members 80 and 82 as was explained with reference to FIGS. 1 and 2.

It should be noted that if one desired, one could construct the disposable garment 10 or 10' such that the chassis 62 is formed from only one or two pieces of material. The material can be a single sheet, a laminate or a composite sandwiched between an outer cover and a bodyside liner. The material can be cut or shaped to provide the desired profile for the disposable garment 10 or 10'.

While the invention has been described in conjunction with several specific embodiments, it is to be understood that many alternatives, modifications and variations will be apparent to those skilled in the art in light of the aforegoing description. Accordingly, this invention is intended to embrace all such alternatives, modifications and variations that fall within the spirit and scope of the appended claims.

We claim:

1. A disposable garment comprising:
    a) a front panel having a first surface, a second surface and a pair of side edges;
    b) a first attachment member secured to said first surface of said front panel and extending beyond said pair of side edges, said first attachment member being a single member having a first side edge, a second side edge and having a width;
    c) a back panel having a first surface, a second surface and a pair of tabs each extending laterally outward in opposite directions, each of said tabs containing a second attachment member located on said second surface;
    d) an absorbent assembly including a liquid pervious bodyside liner, a liquid-impervious outer cover, and an absorbent positioned therebetween, said absorbent assembly further including a first end and a second end, said absorbent assembly being secured to said front panel approximate, said first end and being secured to said back panel approximate said second end, and said absorbent assembly capable of being folded to enable said first and second side edges of said first attachment member to be secured to said pair of tabs to form a waist opening and a pair of leg openings; and
    e) a pair of frangible sections formed in said first attachment member at locations outboard of said pair of side edges of said front panel, each of said pair of frangible sections extending across the width of said first attachment member, and each of said pair of frangible sections being formed of intermittent strength along its length by making some areas stronger than other areas, whereby said pair of tabs can be folded to allow each of said second attachment members to bridge across one of said pair of frangible sections and be removeably secured to said first attachment member to form an easy to open disposable garment.

2. The disposable garment of claim 1 wherein each of said pair of frangible sections is tearable.

3. The disposable garment of claim 2 wherein each of said pair of frangible sections has a linear configuration.

4. The disposable garment of claim 2 wherein each of said pair of frangible sections has a non-linear configuration.

5. The disposable garment of claim 1 wherein each of said second attachment members is a male fastener and said first attachment member is a female fastener.

6. The disposable garment of claim 5 wherein each of said male fasteners contains a plurality of hooks.

7. The disposable garment of claim 5 wherein said female fastener contains a plurality of loops.

8. The disposable garment of claim 1 wherein the width of said first attachment member ranges from between about 1.5 inches to about 8 inches.

9. The disposable garment of claim 1 wherein said first surface is an exterior surface of said disposable garment and said second surface is an interior surface of said disposable garment.

10. The disposable garment of claim 9 wherein said interior surface faces and contacts a wearer's body when said disposable garment is worn.

11. The disposable garment of claim 9 wherein each of said tabs contains a second attachment member located on said interior surface of said disposable garment.

12. The disposable garment of claim 11 wherein each of said second attachment members is a male fastener.

13. The disposable garment of claim 11 wherein each of said second attachment members is a plurality of hooks that will easily engage into a female fastener.

14. The disposable garment of claim 1 wherein said first attachment member is a female fastener.

15. The disposable garment of claim 14 wherein said first attachment member is one or more loops into which a male fastener can engage.

16. The disposable garment of claim 15 wherein each of said tabs are folded over said first attachment member.

17. The disposable garment of claim 1 wherein each of said tabs are folded over said first attachment member.

18. A disposable garment comprising:
    a) a front panel having a first surface, a second surface and a pair of side edges;
    b) a first attachment member secured to said first surface of said front panel and extending beyond said pair of side edges, said first attachment member being a single member having a first side edge, a second side edge and having a width;
    c) a back panel having a first surface, a second surface and a pair of tabs each extending laterally outward in opposite directions, each of said tabs containing a second attachment member located on said second surface;
    d) an absorbent assembly including a liquid pervious bodyside liner, a liquid-impervious outer cover, and an absorbent positioned therebetween, said absorbent assembly further including a first end and a second end, said absorbent assembly being secured to said front panel approximate said first end and being secured to said back panel approximate said second end, said absorbent assembly capable of being folded to enable said first and second side edges of said first attachment member to be secured to said pair of tabs to form a waist opening and a pair of leg openings, and the width of said first attachment member extending from said waist opening to said pair of leg openings; and
    e) a pair of frangible sections formed in said first attachment member, each of said pair of frangible sections located between one of said pair of side edges of said front panel and one of said first and second side edges of said first attachment member, each of said pair of frangible sections extending across the width of said first attachment member, and each of said pair of frangible sections being formed of intermittent strength along its length by making some areas stronger than other areas, whereby said pair of tabs can be folded to allow each of said second attachment members to bridge across one of said pair of frangible sections and be removeably secured to said first attachment member to form an easy to open disposable garment.

19. The disposable garment of claim 18 wherein each of said pair of frangible sections is tearable by a force of less than about 3,000 grams.

20. The disposable garment of claim 18 wherein each of said pair of frangible sections is tearable by a force of from between about 100 grams to about 500 grams.

21. The disposable garment of claim 18 wherein said pair of frangible sections can be simultaneously broken.

22. The disposable garment of claim 18 wherein said absorbent assembly is secured to said first surfaces of both said front and back panels.

23. The disposable garment of claim 18 wherein each of said second attachment members has a width that is less than the width of said first attachment member.

24. A disposable garment comprising:
a) a front panel having a first surface, a second surface and a pair of side edges;
b) a pair of first attachment members secured to said first surface of said front panel and each extending beyond one of said pair of side edges, each of said pair of first attachment members having a first side edge and a second side edge and having a width;
c) a back panel having a first surface, a second surface and a pair of tabs each extending laterally outward in opposite directions, each of said tabs containing a second attachment member located on said second surface;
d) an absorbent assembly including a liquid pervious bodyside liner, a liquid-impervious outer cover, and an absorbent positioned therebetween, said absorbent assembly further including a first end and a second end, said absorbent assembly being secured to said front panel approximate said first end and being secured to said back panel approximate said second end, and said absorbent assembly capable of being folded to enable said pair of first attachment members to be secured to said pair of tabs to form a waist opening and a pair of leg openings; and
e) a pair of frangible sections formed in each of said pair of first attachment members at locations outboard of said pair of side edges of said front panel, each of said pair of frangible sections extending across the width of each of said first attachment members, and each of said pair of frangible sections being formed of intermittent strength along its length by making some areas stronger than other areas, whereby said pair of tabs can be folded to allow each of said second attachment members to bridge across one of said pair of frangible sections and be removeably secured to one of said pair of first attachment members to form an easy to open disposable garment.

25. The disposable garment of claim 24 wherein each of said pair of first attachment members extends from a point below said waist opening to one of said pair of leg openings.

26. The disposable garment of claim 24 wherein each of said pair of first attachment members is permanently secured to one of said pair of tabs at a bond area and each of said pair of frangible sections is positioned laterally inward from one of said bond areas.

27. The disposable garment of claim 26 wherein each of said pair of frangible sections is formed between one of said first locations and one of said pair of side edges of said front panel.

28. The disposable garment of claim 24 wherein said absorbent assembly is secured to said first surfaces of both said front and back panels.

29. A disposable garment comprising:
a) a front panel having a first surface, a second surface and a pair of side edges;
b) a first attachment member secured to said first surface of said front panel and extending beyond said pair of side edges, said first attachment member being a single member having a first side edge, a second side edge and having a width greater than about 0.5 inches;
c) a back panel having a first surface, a second surface and a pair of tabs each extending laterally outward in opposite directions, each of said tabs containing a second attachment member located on said second surface;
d) an absorbent assembly including a liquid pervious bodyside liner, a liquid-impervious outer cover, and an absorbent positioned therebetween, said absorbent assembly further including a first end and a second end, said absorbent assembly being secured to said front panel approximate said first end and being secured to said back panel approximate said second end, and said absorbent assembly capable of being folded to enable said first and second side edges of said first attachment member to be secured to said pair of tabs to form a waist opening and a pair of leg openings; and
e) a pair of frangible sections formed in said first attachment member at locations outboard of said pair of side edges of said front panel, each of said pair of frangible sections extending across the width of said first attachment member, and each of said pair of frangible sections being formed of intermittent strength along its length by making some areas stronger than other areas, whereby said pair of tabs can be folded to allow each of said second attachment members to bridge across one of said pair of frangible sections and be removeably secured to said first attachment member to form an easy to open disposable garment.

30. A disposable garment comprising:
a) a front panel having a first surface, a second surface and a pair of side edges;
b) a first attachment member secured to said first surface of said front panel and extending beyond said pair of side edges, said first attachment member being a single member having a first side edge, a second side edge and having a width greater than about 0.5 inches;
c) a back panel having a first surface, a second surface and a pair of tabs each extending laterally outward in opposite directions, each of said tabs containing a second attachment member located on said second surface;
d) an absorbent assembly including a liquid pervious bodyside liner, a liquid-impervious outer cover, and an absorbent positioned therebetween, said absorbent assembly further including a first end and a second end, said absorbent assembly being secured to said front panel approximate said first end and being secured to said back panel approximate said second end, said absorbent assembly capable of being folded to enable said first and second side edges of said first attachment member to be secured to said pair of tabs to form a waist opening and a pair of leg openings, and the width of said first attachment member extending from said waist opening to said pair of leg openings; and
e) a pair of frangible sections formed in said first attachment member, each of said pair of frangible sections located between one of said pair of side edges of said front panel and one of said first and second side edges of said first attachment member, each of said pair of frangible sections extending across the width of said first attachment member, and each of said pair of frangible sections being formed of intermittent strength along its length by making some areas stronger than other areas, whereby said pair of tabs can be folded to allow each of said second attachment members to bridge across one of said pair of frangible sections and be removeably secured to said first attachment member to form an easy to open disposable garment.

31. A disposable garment comprising:
a) a front panel having a first surface, a second surface and a pair of side edges;
b) a pair of first attachment members secured to said first surface of said front panel and each extending beyond one of said pair of side edges, each of said pair of first attachment members having a first side edge and a second side edge and having a width greater than about 0.5 inches;
c) a back panel having a first surface, a second surface and a pair of tabs each extending laterally outward in opposite directions, each of said tabs containing a second attachment member located on said second surface;
d) an absorbent assembly including a liquid pervious bodyside liner, a liquid-impervious outer cover, and an absorbent positioned therebetween, said absorbent assembly further including a first end and a second end, said absorbent assembly being secured to said front panel approximate said first end and being secured to said back panel approximate said second end, and said absorbent assembly capable of being folded to enable said pair of first attachment members to be secured to said pair of tabs to form a waist opening and a pair of leg openings; and
e) a pair of frangible sections formed in each of said pair of first attachment members at locations outboard of said pair of side edges of said front panel, each of said pair of frangible sections extending across the width of each of said first attachment members, and each of said pair of frangible sections being formed of intermittent strength along its length by making some areas stronger than other areas, whereby said pair of tabs can be folded to allow each of said second attachment members to bridge across one of said pair of frangible sections and be removeably secured to one of said pair of first attachment members to form an easy to open disposable garment.

32. A disposable garment comprising:
a) a front panel having a first surface, a second surface and a pair of side edges;
b) a first attachment member secured to said first surface of said front panel and extending beyond said pair of side edges, said first attachment member being a single member having a first side edge, a second side edge and having a width;
c) a back panel having a first surface, a second surface and a pair of tabs each extending laterally outward in opposite directions, each of said tabs containing a second attachment member located on said second surface, and each of said second attachment members has a width that is less than the width of said first attachment member;
d) an absorbent assembly including a liquid pervious bodyside liner, a liquid-impervious outer cover, and an absorbent positioned therebetween, said absorbent assembly further including a first end and a second end, said absorbent assembly being secured to said front panel approximate said first end and being secured to said back panel approximate said second end, and said absorbent assembly capable of being folded to enable said first and second side edges of said first attachment member to be secured to said pair of tabs to form a waist opening and a pair of leg openings; and
e) a pair of frangible sections formed in said first attachment member at locations outboard of said pair of side edges of said front panel, each of said pair of frangible sections extending across the width of said first attachment member, and each of said pair of frangible sections being formed of intermittent strength along its length by making some areas stronger than other areas, whereby said pair of tabs can be folded to allow each of said second attachment members to bridge across one of said pair of frangible sections and be removeably secured to said first attachment member to form an easy to open disposable garment.

33. A disposable garment comprising:
a) a front panel having a first surface, a second surface and a pair of side edges;
b) a pair of first attachment members secured to said first surface of said front panel and each extending beyond one of said pair of side edges, each of said pair of first attachment members having a first side edge and a second side edge and having a width;
c) a back panel having a first surface, a second surface and a pair of tabs each extending laterally outward in opposite directions, each of said tabs containing a second attachment member located on said second surface, and each of said second attachment members has a width that is less than the width of said first attachment member;
d) an absorbent assembly including a liquid pervious bodyside liner, a liquid-impervious outer cover, and an absorbent positioned therebetween, said absorbent assembly further including a first end and a second end, said absorbent assembly being secured to said front panel approximate said first end and being secured to said back panel approximate said second end, and said absorbent assembly capable of being folded to enable said pair of first attachment members to be secured to said pair of tabs to form a waist opening and a pair of leg openings; and
e) a pair of frangible sections formed in each of said pair of first attachment members at locations outboard of said pair of side edges of said front panel, each of said pair of frangible sections extending across the width of each of said first attachment members, and each of said pair of frangible sections being formed of intermittent strength along its length by making some areas stronger than other areas, whereby said pair of tabs can be folded to allow each of said second attachment members to bridge across one of said pair of frangible sections and be removeably secured to one of said pair of first attachment members to form an easy to open disposable garment.

34. The disposable garment of claim 1 wherein the width of said first attachment member is greater than about 0.5 inches.

35. A disposable garment comprising:
a) a front panel having a first surface, a second surface and a pair of side edges;
b) a first attachment member secured to said first surface of said front panel and extending beyond said pair of side edges, said first attachment member being a single member having a first side edge, a second side edge and having a width greater than about 0.5 inches;
c) a back panel having a first surface, a second surface and a pair of tabs each extending laterally outward in opposite directions, each of said tabs containing a second attachment member located on said second surface, and each of said second attachment members having a width that is less than the width of said first attachment member;

d) an absorbent assembly including a liquid pervious bodyside liner, a liquid-impervious outer cover, and an absorbent positioned therebetween, said absorbent assembly further including a first end and a second end, said absorbent assembly being secured to said front panel approximate said first end and being secured to said back panel approximate said second end, and said absorbent assembly capable of being folded to enable said first and second side edges of said first attachment member to be secured to said pair of tabs to form a waist opening and a pair of leg openings; and e) a pair of frangible sections formed in said first attachment member at locations outboard of said pair of side edges of said front panel, each of said pair of frangible sections extending across the width of said first attachment member, and each of said pair of frangible sections being formed of intermittent strength along its length by making some areas stronger than other areas, whereby said pair of tabs can be folded to allow each of said second attachment members to bridge across one of said pair of frangible sections and be removeably secured to said first attachment member to form an easy to open disposable garment.

36. A disposable garment comprising:

a) a front panel having a first surface, a second surface and a pair of side edges;

b) a first attachment member secured to said first surface of said front panel and extending beyond said pair of side edges, said first attachment member being a single member having a first side edge, a second side edge and having a width greater than about 0.5 inches;

c) a back panel having a first surface, a second surface and a pair of tabs each extending laterally outward in opposite directions, each of said tabs containing a second attachment member located on said second surface, and each of said second attachment members having a width that is less than the width of said first attachment member;

d) an absorbent assembly including a liquid pervious bodyside liner, a liquid-impervious outer cover, and an absorbent positioned therebetween, said absorbent assembly further including a first end and a second end, said absorbent assembly being secured to said front panel approximate said first end and being secured to said back panel approximate said second end, and said absorbent assembly capable of being folded to enable said first and second side edges of said first attachment member to be secured to said pair of tabs to form a waist opening and a pair of leg openings, and the width of said first attachment member extending from said waist opening to said pair of leg openings; and e) a pair of frangible sections formed in said first attachment member, each of said pair of frangible sections located between one of said pair of side edges of said front panel and one of said first and second side edges of said first attachment member, each of said pair of frangible sections extending across the width of said first attachment member, and each of said pair of frangible sections being formed of intermittent strength along its length by making some areas stronger than other areas, whereby said pair of tabs can be folded to allow each of said second attachment members to bridge across one of said pair of frangible sections and be removeably secured to said first attachment member to form an easy to open disposable garment.

37. A disposable garment comprising:

a) a front panel having a first surface, a second surface and a pair of side edges;

b) a pair of first attachment members secured to said first surface of said front panel and each extending beyond one of said pair of side edges, each of said pair of first attachment members having a first side edge and a second side edge and having a width greater than about 0.5 inches;

c) a back panel having a first surface, a second surface and a pair of tabs each extending laterally outward in opposite directions, each of said tabs containing a second attachment member located on said second surface, and each of said second attachment members having a width that is less than the width of said first attachment member;

d) an absorbent assembly including a liquid pervious bodyside liner, a liquid-impervious outer cover, and an absorbent positioned therebetween, said absorbent assembly further including a first end and a second end, said absorbent assembly being secured to said front panel approximate said first end and being secured to said back panel approximate said second end, and said absorbent assembly capable of being folded to enable said pair of first attachment members to be secured to said pair of tabs to form a waist opening and a pair of leg openings; and e) a pair of frangible sections formed in each of said pair of first attachment members at locations outboard of said pair of side edges of said front panel, each of said pair of frangible sections extending across the width of each of said first attachment members, and each of said pair of frangible sections being formed of intermittent strength along its length by making some areas stronger than other areas, whereby said pair of tabs can be folded to allow each of said second attachment members to bridge across one of said pair of frangible sections and be removeably secured to one of said pair of first attachment members to form an easy to open disposable garment.

* * * * *